United States Patent
Skands et al.

(10) Patent No.: US 6,996,260 B1
(45) Date of Patent: Feb. 7, 2006

(54) ANALYSIS OF FUNDUS IMAGES

(75) Inventors: Ulrik Skands, Tureby (DK); Michael Grunkin, Skodsborg (DK); Michael Edberg Hansen, Lyngby (DK)

(73) Assignee: Retinalyze Danmark A/S, Hellerup (DK)

( * ) Notice: Subject to any disclaimer, the term of this patent is extended or adjusted under 35 U.S.C. 154(b) by 0 days.

(21) Appl. No.: 09/959,428

(22) PCT Filed: Apr. 18, 2000

(86) PCT No.: PCT/EP00/03507

§ 371 (c)(1),
(2), (4) Date: Dec. 28, 2001

(87) PCT Pub. No.: WO00/65982

PCT Pub. Date: Nov. 9, 2000

(30) Foreign Application Priority Data

Apr. 29, 1999 (GB) .................................... 9909966

(51) Int. Cl.
*G06K 9/00* (2006.01)
(52) U.S. Cl. ...................................... 382/128; 382/117
(58) Field of Classification Search ................ 382/128, 382/117, 258, 259; 351/206; 396/18
See application file for complete search history.

(56) References Cited

U.S. PATENT DOCUMENTS 5,270,924 A * 12/1993 Hideshima .................. 382/117
6,053,865 A * 4/2000 Sugiyama et al. ........... 600/300

OTHER PUBLICATIONS

Y.A. Tolias et al., IEEE Transactions on Medical Imaging, vol. 17, No. 2 (1998) pp. 263-273.
K. Akita et al., Pattern Recognition, vol. 15, No. 6 (1982) pp. 431-443.
R. Giansanti et al., Conference Publication No. 443 (1997) pp. 530-534.
T. Kurokawa et al., Electronics Letters, vol. 34, No. 10 (1998) pp. 976-977.
J. K. Kristinsson et al., Scandinavica: The Ophthalmological Journal of the Nordic Countries, Supplement 223, vol. 75 (1997) pp. 1-76.

(Continued)

*Primary Examiner*—Jingge Wu
*Assistant Examiner*—A. Upreti
(74) *Attorney, Agent, or Firm*—Birch, Stewart, Kolasch & Birch, LLP

(57) ABSTRACT

A method of processing an image includes processing the image so as to produce a modified image in which the width of each line object is a single pixel, identifying pixels of the modified image which are relocated on a line object, and allocating to each image point a score value dependent upon the number of adjacent pixels which are likewise located on a line, determining from the score values which of the image points is disassociated with a crossing point or a bifurcation of the respective line object, performing a matching operation on pairs of line segments for each crossing point, classifying the line objects in the original image into two arbitrary sets, and designating one of the sets as representing venous structure, the other of the sets as representing arterial structure.

10 Claims, 1 Drawing Sheet

OTHER PUBLICATIONS

P. H. Gregson et al., Computers and Biomedical Research, vol. 28 (1995) pp. 291-304.

L. Pedersen et al., Pattern Recognition Letters, vol. 21 (2000) pp. 1215-1223.

J. A. Kylstra et al., Ophthalmology, Springer-Verlag (1986) pp. 477-480.

S. Chaudhuri et al., IEEE Transactions on Medical Imaging, vol. 8, No. 3 (1989) pp. 263-269.

I. Ragnemalm, Department of Electrical Engineering, Linkoping University, "Rotation invariant skeletonization by thinning using anchor points" pp. 227-241.

B. Kruse, Department of Electrical Engineering, Linkoping University, "An exact sequential Euclidean distance algorithm with application to skeletonizing" (1991) pp. 982-992.

B. Kochner et al., SPIE, vol. 3338 (1998) pp. 755-761.

Z. Liu et al., IEEE/EMBS (1997) pp. 524-525.

Y. A. Tolias et al., IEE Transactions on Medical Imaging, vol. 17, No. 2 (1998) pp. 263-273.

Akita K et al.: "A computer method of understanding ocular dundus images" vol. 15, No. 6, pp. 431-443 (1982) XP002131982.

Zheng L et al.: " Automatic image analysis of fundus photograph" vol. 2, pp. 524-525 1997.

Kochner B et al.: "Course tracking and contour extraction of retinal vessels from color fundus photographs: most efficient use of steerable filters for model based image analysis" vol. 2238, pt. 1-2 pp. 755-761, XP00213979 (1998).

Tolias Y A et al.: " A fuzzy vessel tracking algorithm for retinal images based on fuzzy clustering" vol. 17 No. 2, pp. 263-273 XP002131981 (1998).

Giansanti R et al.: "Imaging system for retinal change evaluation" vol. 2, pp. 530-534 XP002131983 (1997).

Kurokawa T. et al.: "Maze-tracing algorithm applied to eye-fundus blood vessels" vol. 34, No. 10, pp. 976-977 XP002131984 (1998).

\* cited by examiner

ANALYSIS OF FUNDUS IMAGES

This application is the national phase under 35 U.S.C. § 371 of PCT International Application No. PCT/EP00/03507 which has an International filing date of Apr. 18, 2000, which designated the United States of America and was published in English.

BACKGROUND OF THE INVENTION

1. Field of the Invention

This invention relates to the detection and analysis of blood vessels, and is of particular application in the analysis of blood vessels in images of the ocular fundus (the back of the eye), hereinafter referred to as the fundus. The analysis of blood vessels in the fundus is important because the fundus is one of the few places in the body where blood vessels can be easily observed, and such observation is therefore a very convenient way of monitoring certain diseases associated with circulation defects, in particular arteriosclerosis, hypertension and diabetes.

2. Description of Background Art

Particular pathological manifestations which it is useful to monitor are features such as venous beading, focal arteriolar narrowing and generalized arteriolar narrowing. Measurement of these quantities requires very precise measurements of the caliber of the blood vessels. Hence, a precise knowledge of both localization and orientations of the vessels is important. Additional features, which are of interest in fundus images are micro-aneurysms and exudates, which show up on fundus images as generally "dot shaped" (i.e., circular, or approximately circular) areas. It is also of interest to be able to distinguish between such micro-aneurysms and exudates, and to distinguish them from other "dot shaped" pathologies in the image, e.g., so-called "cotton wool spots" and hemorrhages. In particular, it is desirable to determine the position of the dot shaped pathology relative to the vascular structure.

Currently, examination of fundus images is carried out principally by a clinician examining each image "manually". This is not only very time-consuming, since even an experienced clinician can take several minutes to assess a single image, but is also prone to error since there can be inconsistencies between the way in which different clinicians assess a given image.

It is therefore desirable to provide ways of automating the process of the analysis of fundus images, using computerized image analysis, so as to provide at least preliminary screening information and also as an aid to diagnosis to assist the clinician in the analysis of difficult cases.

A number of steps are necessary to carry out such analysis. In general, it is necessary first to segment the fundus image into blood vessels and background. Visually, vessels in the fundus image appear as dark lines on a relatively uniform bright background. Various methods are known for segmenting the fundus image. Reference is made, for Example to the following:—

Tolias y a et al "A fuzzy vessel tracking algorithm for retinal images based on fuzzy clustering, IEEE Transactions On Medical Imaging, April 1998, IEEE, USA, vol. 17, no. 2, pages 263–273, ISSN: 0278–0062;

Akita k et al: "A computer method of understanding ocular fundus images" Pattern Recognition, 1982, UK, vol. 15, no. 6, pages 431–443, ISSN: 0031-3203 chapter 4;

Giansanti r et al: "Imaging system for retinal change evaluation" Sixth International Conference on Image Processing and its Applications (conf. publ. NO. 443), Proceedings of 6th International Conference on Image Processing and its Applications (conf publ. no. 443), Dublin, Ireland, 14–17 July 1997, pages 530–534 vol. 2, 1997, London, UK, IEE, UK ISBN: 0-85296-692-X chapter 2; and Kurokawa T et al: "Maze-tracing algorithm applied to eye-fundus blood vessels" Electronics Letters, 14 MAY 1998, IEE, UK, vol. 34, no. 10, pages 976–977, ISSN: 0013-5194.

Next, it is generally desirable to provide a method of determining accurately, using computerized image analysis techniques, the position of both the papilla (the point of exit of the optic nerve) and the fovea (the region at the center of the retina, where the retina is most sensitive to light).

Having identified the blood vessels in the image, it is desirable to be able to distinguish between veins and arteries among the blood vessels. This can be important, for example in the diagnosis of venous beading and focal arteriolar narrowing.

The vascular system observed in the ocular fundus images is by nature a 2-dimensional projection of a 3dimensional structure. It is quite difficult in principle to distinguish veins from arteries, solely by looking at isolated vessel segments. However, we have discovered that effective separation can be achieved by making use of the fact that, individually, the artery structure and the vein vessel structures is each a perfect tree, (i.e., there is one unique path along the vessels from the heart to each capillary and back).

On the retina, the artery and vein structures are each surface filling, so that all tissue is either supplied or drained by specific arteries or veins, respectively.

SUMMARY OF THE INVENTION

The method according to the invention for distinguishing veins from arteries is based on the realization that crossings of vessel segments are, for practical purposes, always between a vein and an artery (i.e., crossings between arteries and arteries or between veins and veins are, for practical purposes, non-existent). This realization is based on an intuitive realization that it is apparent that if two independent tree systems are both surface filling and originate from the same point (the papilla) and only a limited number of bifurcations are allowed, some crossings between the two systems must occur.

In accordance with a first aspect of the invention, there is provided a method of processing an image comprising a plurality of line objects representative of superposed arterial and venous blood vessels, so as classify the said objects as respective arterial or venous vessels which method comprises: processing the image so as to produce a modified image in which the width of each said line object is a single pixel, identifying pixels of the said modified image which relocated on a line object, and allocating to each said image point a score value dependent upon the number of adjacent pixels which are likewise located on a line, determining from the said score values which of the said image points disassociated with crossing point or a bifurcation of the respective line object, wherein a crossing point is represented by an image point which is the intersection of four line segments, performing a matching operation on pairs of said line segments for each said crossing point, to determine the path of blood vessels in the image, thereby classifying the line objects in the original image into two arbitrary sets, and thereafter designating one of the sets as representing venous structure, the other of the sets as representing arterial structure, depending on one or more of the following criteria:

a) complexity of structure;
b) average density;
c) average width;
d) tortuosity; and
e) vessel length.

Various known methods can be used to classify the image sets according to structure complexity, average density, average width, and tortuosity.

For example a measure of structure complexity may be computed as the number branch- and/or endpoints divided by the total number of pixels in the structure. The higher this ratio the higher is the structure complexity. The term "structure" is intended to mean a connected subset of the total vascular network, which haste assigned the same arbitrary label.

Average density may be measured as the average pixel intensity, for one or more vessel segments in a given structure. The average pixel intensity can be measured along the skeletonized (single pixel wide) vessel line or in the full image (i.e., the image prior to skeletonization).

Various methods are known for assessing average vessel width, for example, the methods of:

J. K. Kristinsson (1997), "Diabetic Retinopathy-Screening and Prevention of Blindness", Doc. Thesis, Acta Ophthalmologica Scandinavica, Suppl. 223, p. 76., P. H. Gregson, et. al. (1995), "Automated Grading of Venous Beading", Computers and Biomedical Research, 28,291–304; and L. Pedersen, et. al. (1999), Quantitative Measurement of Changes in Retinal Vessel Diameter binocular Fundus Images, In Proc. 11$^{th}$ Scandinavian Conference on Image Analysis SCIA 99, vol. 1, Kangerlussuaq, Greenland, pp. 439–446.

Similarly, various methods are known which can be employed for determining tortousity, for example the method of J. A. Kylstra, E. Stefansson, et. al. (1986), "The Relationship Between Retinal Vessel Tortuosity, Diameter, and Transmural Pressure", Graefe's Arch Clin. Exp. Ophthalmol., 224: 477–480. Tortousity is essentially a measure of the length ratio of the straight line length between two arbitrary points on a vessel to the length between the same points measured along the course of the vessel. If the ratio is close to 1, the vessel is straight, and the closer to 0 the ratio approaches, the more tortuous the vessel.

The precise method employed in each case is not critical, since all that is required is a comparison of the property, for the two identified sets of blood vessel "trees."

In a further aspect of the invention, we have discovered that the usefulness and reliability of various measurements of image features can be improved significantly by employing the distance between the papilla and the fovea as an internal calibration for the measurement of various image features. In particular, a further aspect of the invention provides a method of determining the size of image features in the analysis of an image of a fundus, which method comprises:

determining the position of a first point, representing the center of the papilla;
determining the position of a second point, representing the center of the fovea;
measuring the distance between the first point and the second point; and
employing the said distance as a size calibration standard in the investigation of features of the said fundus image.

The papilla and fovea are easily recognized morphological elements in the retina, as described, for example, in Duke-Elder, Stewart: System of Ophthalmology, vol. II, The Anatomy of the Visual System. Henry Kimpton Publishers, London, 1961.

The respective positions of the papilla and fovea may be determined by the interactive examination of a fundus image, for example using a screen and pointing device (e.g., a mouse) and interactively placing a first disc over the fovea, and a second disc over the papilla on the fundus image. The respective discs may be sized and placed manually using the mouse, a computer being used to measure distance between the centers of the circles, and thereby the distance from the center of the papilla to the center of the fovea. Other methods may be used, in particular, methods providing a greater degree of automation. For example, a good estimate of the position of the papilla in a fundus image can be obtained by representing the image features representing blood vessels as a plurality of points, each point being represented by a pair of (x, y) coordinates, and fitting the (x, y) pairs of co-ordinates to an equation of the form, $$Y=a_0+a_1x+a_2x^2\ldots+a_nx^n \qquad \text{(Equation A)}$$

(wherein n is at least 2, and preferably wherein n is 2) to determine the value of coefficients $a_0$ to $a_n$.

Having fitted the (x, y) pairs to Equation A, a turning point of the equation is then determined, and the papilla is identified from the location of the turning point in the fundus image.

An additional step may also be employed, in which template matching is applied to the region of the image containing the turning point. The template employed is circular, or at least approximately circular, and corresponds in size to the approximate anticipated size of the papilla. Correlation techniques between the said image region and the appropriate template can be used to obtain a more accurate determination or the center of the papilla. The template employed is preferably a ring template or a disc template, having assize of approximately 1500 micrometers.

A similar technique can be employed in order to determine the position of the fovea. In accordance with this method, the image features representing blood vessels are again represented as a plurality of points, each point being represented by a pair of (x, y) co-ordinates, and the (x, y) pairs of co-ordinates are fitted to an equation of the form, $$Y=a_0+a_1x+a_2x^2\ldots+a_nx^n \qquad \text{(Equation A)}$$

(wherein n is at least 2, and preferably wherein n is 2) to determine the value of coefficients $a_o$ to $a_n$.

In order to estimate the position of the fovea, the equation may be used to determine the position of at least two straight lines, which are perpendicular to the curve represented by the equation. The point of intersection of the straight lines is then used to identify the location of the fovea in the image.

Again, an additional step may be employed, in which template matching is applied to the region of the image containing the said point of intersection. The template employed is circular, or at least approximately circular, and corresponds in size to the approximate anticipated size of the fovea. Correlation techniques (as described in more detail below) between the said image region and the appropriate template can be used to obtain a more accurate determination of the center of the fovea. Use may also be made of the fact that the fovea is positioned approximately 3000 um from the center of the papilla, and approximately 5 degrees below it (as mentioned in the Duke-Elder reference mentioned above).

The template employed for locating the fovea is preferably a ring template or a disc template, having a size of approximately 1000 micrometers.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
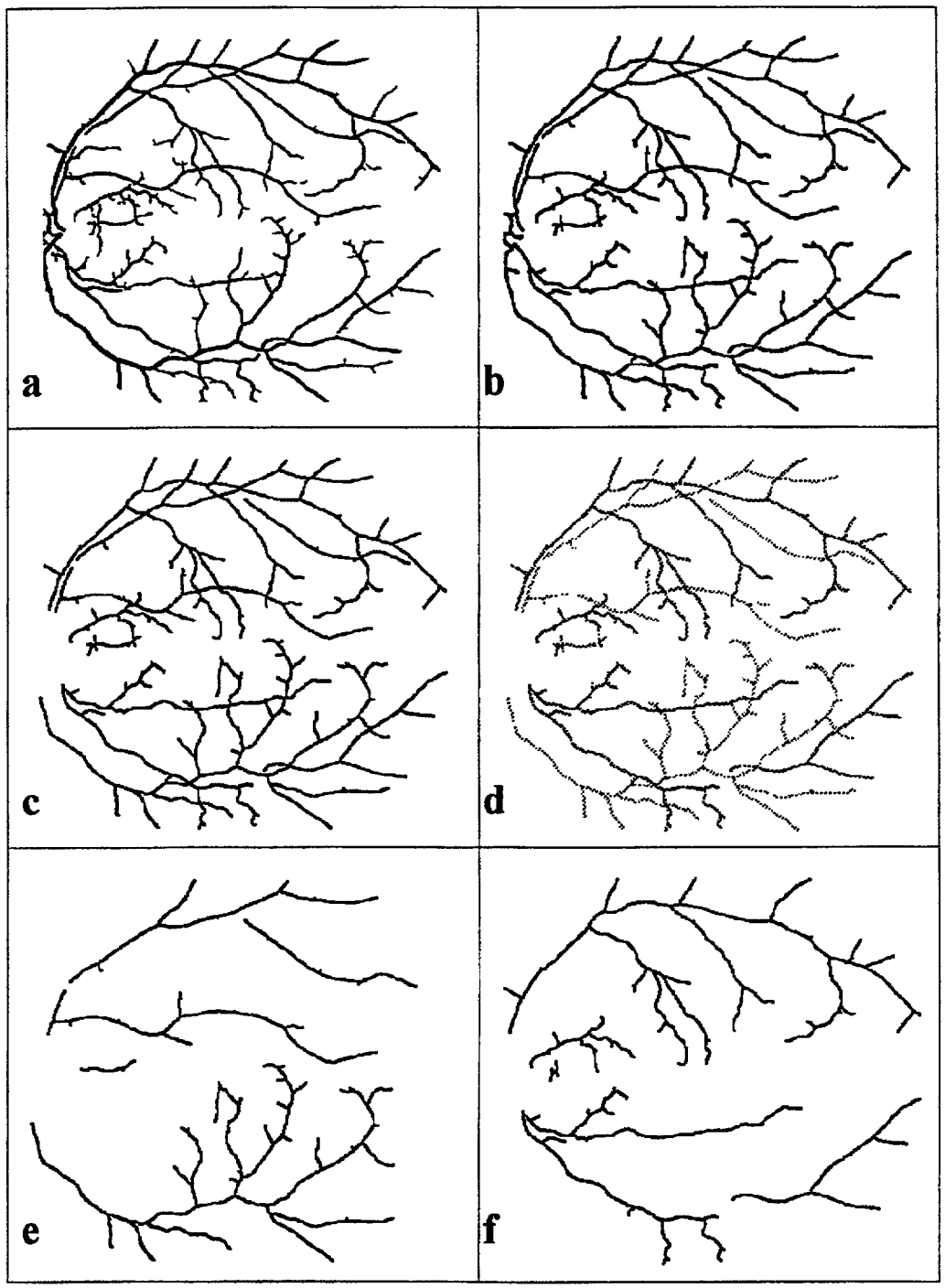
FIGS. 1a to 1f are graphical representations of the steps involved in retrieving the connected components of the vascular structure in digitized ocular fundus images.

A number of preferred embodiments of the invention will now be described with reference to the accompanying FIG. 1, which is a graphical representation of vascular structure in a digitized ocular fundus image, and illustrates how the arterial and venous systems may be derived from the image.

Finding the Arteriolar and Venous Systems

Various methods are known by which the vascular system may be isolated from the rest of the image content and skeletonized. For example a method may be employed based on the one described in the article by Subhasis Chaudhuri et al, "Detection of Blood Vessels in Retinal Images Using Two-Dimensional Matched Filters", IEEE Transactions on Medical Imaging, Vol. 8, No. 3, September 1989. In this method, use is made of the fact that the vessels are linear in a local neighborhood, where different filter matrices have different orientations. The localization and orientation of such line elements may be determined using a template matching approach (sometimes referred to as match filters). Alternatively, a method may be employed based on the method of Akita, referred to above.

Skeletonization

In order to facilitate the analysis of the bi-level image, where the two classes primarily represents vessel structures and background, it is desirable to reduce the object class representing vessels to a single pixel in width. This representation is most convenient in the quantitative and structural analysis of the vascular bed that follows. The process itself is called skeletonization (or thinning), and the general principles of the technique are well known and documented in image processing.

The preferred method of skeletonization is the method referred to as the Medial Axis Transform (MAT) (I. Ragnemalm (1993), "Rotation invariant skeletonization by thinning using anchorpoints", $8^{th}$ Scandinavian Conf. On Image Analysis, Tromsø). Ragnemalm describes a distance propagated skeletonization which ensures that the skeleton always falls on the center of the object.

In order to prevent the thinning algorithm from pruning too much important structural information, reference points in the skeleton have to be determined. Ragnemalm calls these points anchor points. Anchor points can never be removed in the thinning process. In accordance with the method suggested by Ragnemalm, the α-skeleton algorithm suggested by Kruse may also be used to generate the anchor points (B. Kruse (1991), "An exact sequential Euclidean distance algorithm with application to skeletonizing", Proc., $7^{th}$ Scandinavian Conf. on Image Analysis, pp. 982–992). The skeleton is generated by systematically checking and pruning object pixels from increasing distance classes by using the algorithm described above.

In general, a pixel will be removed only if it does not cause a lack of connectivity. Preferably however a pixel is always removed if it is closer than 3 pixels from the edge of the object. This ensures a limited level of complexity in the resulting skeleton.

FIG. 1 is a graphical representation of the steps involved retrieving the connected components of the vascular structure in digitized ocular fundus images. In FIG. 1, the lines of the single pixel wide skeletonized graph have been expanded to a uniform width, for clarity.

FIG. 1a shows the total vascular structure as a binary image. This is the immediate result of a threshold processing. FIG. 1b shows a skeletonized result using the Medial Axis Transform (MAT). In FIG. 1c, the optic disc has been delineated and masked out, as the vascular structure within the optic disc is not suitable for subsequent analysis. In FIG. 1d, connected components of the vascular system have been identified and shown in different shades of gray independently for the superior and the inferior temporal part of the structure. FIG. 1e shows a binary representation of the connected component designated class A. FIG. 1f shows a binary representation of the connected component designated class B.

Having isolated the vascular system, it is desirable to distinguish the between arterial and venous blood vessels.

As indicated above, the vascular system observed in the ocular fundus images is by nature a 2-dimensional projection of a 3-dimensional structure. Our method is based on the realization that effective separation can be achieved by making use of the fact that, individually, the artery structure and the vein vessel structures is each a perfect tree, (i.e., there is one unique path along the vessels from the heart to each capillary and back). The method according to the invention for distinguishing veins from arteries is based on the realization that crossings of vessel segments are, for practical purposes, always between a vein and an artery (i.e., crossings between arteries and arteries or between veins and veins are, for practical purposes, non-existent).

In an initial step, the image is processed to identify certain characteristic points in the skeletonized vessel structure. Of particular interest are endpoints, branch-points, and crossings defining the connectivity and complexity of the graph. These are identified by having 1, 3, and 4 neighbors, respectively. Pixels having precisely 2 neighbors are defined as normal segment pixels.

At a crossing point, for two vessel segments to cross, one of them must pass under the other and continue on the other side. This means that when we see a crossing vessel pair in a digitized and skeletonized image, four vessel segments will project from the crossing point, and will have to constitute two matched pairs. In most cases, opposite segments are paired (indicating a simple vessel crossing), however in some cases a vein will re-emerge on the same side of an artery (and vice-versa). It is therefore necessary to pair elements at a crossing point by assigning matching labels to the segments that belong together. Pairing can be done by investigating various properties of the crossing point, and in particular, by 1. Comparing the width of the blood vessels entering the crossing point in the original (i.e., non-skeletonized) image. It is to be noted that veins are on average somewhat wider than arteries, and so it is not unusual for noticeable differences in width to be discernible.
2. Measuring the crossing angle. It is found empirically that vessel-branching never takes place at an angle of more than 90 degrees.
3. Measure the average density of the blood vessels in the non-skeletonized image. It is to be noted that veins are on the average darker than arteries.

After the vessels entering each crossing point have been paired satisfactorily, the vessels in the entire image may be labeled. By starting at an arbitrary crossing point, assign one of two possible labels to one of the crossing pairs and the opposite color to the other crossing pair, and propagating these labels successively throughout the entire tree. FIG. 1d shows the result of carrying out this method on the skeletonized image of FIG. 1c. The connected components in FIG. 1d are shown with the same shade of gray are extracted and shown in the binary plots of FIGS. 1e and 1f.

One difficulty observed with this method is that there is no unique solution to the labeling problem, and arbitrary choices have to be made in certain cases of branch configurations. Starting from different crossing points may therefore give rise to different results. However, the difficulty which arises in practice is small.

In a preferred embodiment of the method, segments are labeled first with preliminary values. Once a segment has been labeled it cannot be assigned another (preliminary) label. The preliminary labels are propagated out through the tree. When labeling propagation fronts meet, a choice is made as to which connected sub-tree should keep its preliminary labels ("the winner"). The segments of the "loser" are re-labeled by back-propagation. This algorithm is more complex, but prevents false labeling to propagate too far out through the graph.

Once the connected components of the vascular systems have been identified, features can be derived so that the trees identified can be designated a final label of either "venous" or "arterial". Features, from isolated vessel segments, which may be used for such a determination, are for example:

1) average densities;
2) average widths; and
3) tortuosity;

Features can also be related to the connected component graph itself. Usually the artery graph has less complexity (is simpler to look at) than the corresponding venous graph, and that the average length of vessel segments in artery arcades is longer than the average length in venous segments. Also, the total length of a venous arcade is usually longer than the corresponding artery arcade.

Various methods for determining these quantities are known, for example from J. A. Kylstra, E. Stefansson, et. al. (1986), "The Relationship Between Retinal Vessel Tortuosity, Diameter, and Transmural Pressure", Graefe's Arch Clin. Exp. Ophthalmol., 224: 477–480., J. K. Kristinsson (1997), "Diabetic Retinopathy-Screening and Prevention of Blindness", Doc. Thesis, Acta Ophthalmologica Scandinavica, Suppl. 223, p. 76., and John C. Russ (1991), Computer-Assisted Microscopy, Plenum Publ. Corp., New York, p. 453.

The various quantities used to distinguish venous from arterial structure may be used separately, or in combination.

Locating the Papilla and Fovea

Having located the position of the blood vessels in the fundus image, it is of considerable importance to locate accurately the position of the papilla and fovea.

The fovea and the papilla are two of the most important anatomical elements of the retina. Sight threatening lesions are connected to both of them, and they constitute together with the vascular system the basis of orientation in the retina, as described, for example, in Duke-Elder, Stewart: System of Ophthalmology, vol. II, The Anatomy of the Visual System. Henry Kimpton Publishers, London, 1961.

As indicated above, in accordance with one aspect of the invention, the distance between the center of the fovea and the center of the papilla can be used as a reference length for normalizing all distances in the image. It has been found that the use of this technique minimizes intra-subject variability, and is highly desirable if quantitative measurements are to be performed in the vascular systems or if the size of pathologies is important.

In accordance with one aspect of the invention, the location of the papilla can be estimated to a reasonable degree of accuracy by matching a function of at least second order (typically a conic function) to the thickest vessels segments. It can safely be assumed that the vessels that are the thickest enter and exit the retina through the papilla.

This approach works whether or not the papilla is present in the image. The approximation which is obtained to the position of the center of the papilla is fairly coarse, but nevertheless is sufficiently accurate for some purposes, and also provides a useful starting point for more refined techniques, such as template matching or circular Hough transform methods (as described, for example, in M. Sonka, et. al. (1993), "Image Processing, Analysis and Machine Vision", Chapman & Hall, London, p. 555).

A better approximation can generally be obtained by subsampling the image in the region indicated by the parameter matching technique, and employing a circular template matching method using, for example, the correlation algorithms described above, utilizing templates (ring or disc) of the typical size of the papilla. The diameter of the papilla is typically 1500 micrometers.

A similar technique can be employed to locate the position of the center of the fovea in the image, but instead of the turning point of the curve, the point of intersection of two or more points normal to the curve is taken as a coarse approximation to the position of the fovea. As with the papilla, the approximation can be improved by subsampling the image in the region indicated by the parameter matching technique, and employing a circular template matching method using, for example the correlation algorithms described above, utilizing templates (ring or disc) of the typical size of the fovea.

An alternative method for location of the fovea in the image relies on the fact that the fovea generally lies between two large temporal vessel arcades, and approximately 3,000 micrometers from the center of the papilla. Also, if the fovea is clearly visible in the image, it is represented as a large local density minimum.

It should be understood that the various aspects of the invention described above may be employed alone or together in various combinations, and the scope of the invention should be construed accordingly.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of processing an image comprising a plurality of line objects representative of superposed arterial and venous blood vessels, so as to classify the line objects as respective arterial or venous vessels, said method comprising the steps of:
- processing the image so as to produce a modified image in which the width of each said line object is a single pixel;
- identifying pixels of the modified image which are located on a line object, and allocating to each said image point a score value dependent upon the number of adjacent pixels which are likewise located on a line;
- determining from the score values which of the image points is associated with a crossing point or a bifurcation of the respective line object, wherein a crossing point is represented by an image point which is the intersection of four line segments;
- performing a matching operation on pairs of said line segments for each said crossing point, to determine the path of blood vessels in the image, thereby classifying the line objects in the original image into two arbitrary sets, and thereafter designating one of the sets as representing venous structure, the other of the sets as representing arterial structure, depending on one or more of the following criteria:
  a) complexity of structure;
  b) average vessel density;
  c) average vessel width;
  d) vessel tortuosity; and
  e) vessel length.

2. The method according to claim 1, wherein the modified image in which the width of each said line object is a single pixel, is produced by defining anchor points in the thinning process and ensuring that anchor points are not removed during thinning.

3. The method according to claim 1, wherein a crossing point is defined as an image point having 4 neighbor pixels.

4. The method according to claim 1, wherein a bifurcation is defined as an image point having 3 neighbor pixels.

5. The method according to claim 1, wherein the matching operation comprises pairing opposite line segments as belonging to the same vessel.

6. The method according to claim 1, wherein the matching operation comprises comparing in a non-modified image the width of vessel segments, said vessel segments each corresponding to the line segments in the crossing point.

7. The method according to claim 1, wherein the matching operation comprises measuring the average vessel density of blood vessels in a non-modified image and in the non-modified image comparing the density of vessel segments with the average vessel density, said vessel segments each corresponding to the line segments in the crossing point.

8. The method of claim 1, wherein the designation of the sets depends on the one or more the following criteria:
- complexity of structure;
- average width;
- tortuosity; and
- vessel length.

9. The method of claim 1, wherein the designation of the sets depends on the relative complexity of the two sets.

10. The method of claim 1, wherein the designation of the sets depends on the total vessel lengths of the two sets or the average length of all segments in each of the sets.

* * * * *